US009651687B2

United States Patent
Watson (10) Patent No.: US 9,651,687 B2
(45) Date of Patent: May 16, 2017

(54) POSITRON ATTENUATION TOMOGRAPHY (71) Applicant: Siemens Medical Solutions USA, Inc., Malvern, PA (US)

(72) Inventor: Charles C. Watson, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 14/880,494

(22) Filed: Oct. 12, 2015

(65) Prior Publication Data

US 2016/0116614 A1 Apr. 28, 2016

Related U.S. Application Data (60) Provisional application No. 62/067,094, filed on Oct. 22, 2014.

(51) Int. Cl.
*G01T 1/29* (2006.01)
*A61B 6/00* (2006.01)
*A61B 6/03* (2006.01)
*A61B 5/055* (2006.01)
*A61B 5/00* (2006.01)
*G01R 33/48* (2006.01)

(52) U.S. Cl.
CPC .......... *G01T 1/2985* (2013.01); *A61B 5/0035* (2013.01); *A61B 5/055* (2013.01); *A61B 6/037* (2013.01); *A61B 6/4417* (2013.01); *A61B 6/4429* (2013.01); *A61B 6/5205* (2013.01); *G01R 33/481* (2013.01)

(58) Field of Classification Search
CPC ..... G01T 1/2985; A61B 5/0035; A61B 5/055; A61B 6/037; A61B 6/4417
See application file for complete search history.

(56) References Cited

U.S. PATENT DOCUMENTS

| 2011/0103669 A1* | 5/2011 | Michel | G06T 11/005 382/131 |
|---|---|---|---|
| 2013/0322715 A1* | 12/2013 | Wollenweber | A61B 5/055 382/131 |
| 2014/0228673 A1* | 8/2014 | Watson | A61B 6/5247 600/411 |

OTHER PUBLICATIONS

Alessio, Adam, and Lawrence MacDonald. "Spatially variant positron range modeling derived from CT for PET image reconstruction," in Nuclear Science Symposium Conference Record, 2008. NSS '08. IEEE , vol., No., pp. 3637-3640, Oct. 19-25, 2008.
Bai, B., Ruangma, A., Laforest, R., Tai, Y. C., & Leahy, R. M., "Positron range modeling for statistical PET image reconstruction." In Nuclear Science Symposium Conference Record, (vol. 4, pp. 2501-2505), Oct. 2003.
Derenzo, Stephen E. "Mathematical removal of positron range blurring in high resolution tomography." Nuclear Science, IEEE Transactions on 33.1 (1986): 565-569.

(Continued)

*Primary Examiner* — Casey Bryant (57) ABSTRACT

Positron attenuation is estimated. Positrons attenuate differently than x-rays, so measuring positron attenuation may assist in diagnosis or material study. To measure positron attenuation, a positron beam is formed using a magnetic field. The annihilations along the beam within an object are measured using positron emission tomography. The rate of annihilation and integration of the rate of annihilation along the positron beam may be used to determine positron attenuation.

18 Claims, 6 Drawing Sheets

(56) References Cited

OTHER PUBLICATIONS

Herzog, Hans, et al. "Influence from high and ultra-high magnetic field on positron range measured with a 9.4TMR-BrainPET," in Nuclear Science Symposium Conference Record (NSS/MIC), 2010 IEEE, vol., No., pp. 3410-3413, Oct. 30, 2010-Nov. 6, 2010.
Knoll, Glenn F. Radiation detection and measurement. John Wiley & Sons, pp. 44-50, 2010.
Levin, Craig S., and Edward J. Hoffman. "Calculation of positron range and its effect on the fundamental limit of positron emission tomography system spatial resolution." Physics in medicine and biology 44.3 (1999): 781-799.
Martin, James E. Physics for radiation protection. John Wiley & Sons, pp. 234-237, 2013.
Polity, A., et al. "Defects in electron-irradiated Si studied by positron-lifetime spectroscopy." Physical Review B vol. 58, Issue 16. Oct. 15, 1998.
Watson, Charles C., Lars Eriksson, and Armin Kolb. "Physics and applications of positron beams in an integrated PET/MR." Physics in medicine and biology 58.3 (2013).

\* cited by examiner

POSITRON ATTENUATION TOMOGRAPHY

RELATED APPLICATIONS

This application claims the benefit of U.S. Provisional Application No. 62/067,094 filed on Oct. 22, 2014, the entire contents of which are hereby incorporated by reference.

BACKGROUND

The present embodiments relate to positron tomography. In positron emission tomography (PET), a radiopharmaceutical is placed within a patient. The radiopharmaceutical tags particular biological function. Positrons emitted by the radiopharmaceutical at the tagged locations interact with nearby electrons, causing detectable radiation. The PET scanner detects the annihilation events. Using tomography, a distribution of rates of annihilation is created. This reconstruction represents the tagged biological activity in the patient, but provides little information about the tissues of the patient other than biological activity.

PET may be combined with another imaging modality in a hybrid system. The other modality provides additional tissue information. PET/computed tomography (CT), single photon emission computed tomography (SPECT)/CT, and PET/magnetic resonance (MR) multimodality imaging systems allow scans to be performed back-to-back or in a same coordinate system and similar timing. The axial fields of view of the individual modalities are as close together as possible in order to minimize the impact of patient motion and increase correlation of the respective data sets. While the CT or MR may provide different tissue information than PET or SPECT, further information may assist in diagnosis.

BRIEF SUMMARY

By way of introduction, the preferred embodiments described below provide additional information in the form of positron attenuation. Positrons attenuate differently than x-rays, so measuring positron attenuation may assist in diagnosis. To measure positron attenuation, a positron beam is formed using a magnetic field. The annihilations along the beam within an object are measured using PET. The rate of annihilation and integration of the rate of annihilation along the positron beam may be used to determine positron attenuation.

In a first aspect, a positron attenuation tomography system includes a magnet operable to generate a magnetic field through an object. A positron source is positioned relative to the magnetic field so that a positron beam extends into the object. A positron emission tomography system is configured to detect annihilation events of the positron beam interacting with the object and to reconstruct a spatial distribution of the annihilation events. A processor is configured to estimate linear attenuation coefficients of the object along the positron beam from the spatial distribution of the annihilation events.

In a second aspect, a method is provided for positron attenuation tomography. Positrons directed along magnetic field lines through a bore of a ring of photon detectors are generated. An annihilation rate for the positrons at a location in material is detected with the ring of photon detectors. A positron attenuation coefficient for the location is estimated from the annihilation rate. A property of the material is indicated with the positron attenuation coefficient.

In a third aspect, a hybrid magnetic resonance and positron emission tomography system is provided. A bore is shared by a magnetic resonance system and a positron emission tomography system. A processor is configured to determine positron attenuation in a patient within the bore. The positron attenuation is determined by calculation using annihilation radiation emissions measured by the positron emission tomography system in response to a transmitted beam of positrons into the patient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The attenuation coefficients of magnetically constrained positron beams in matter are imaged. A magnetically constrained $\beta^+$-ray beam may maintain spatial coherence over three orders of magnitude attenuation in matter while signaling intensity via the generated annihilation radiation. Non-destructive imaging of the linear attenuation coefficients (LACs) of positron beams in heterogeneous materials is possible. A positron emission tomography (PET) system embedded within a uniform static magnetic field, such as exists in some hybrid PET/magnetic resonance imaging (MRI) scanner, is used. A $^{68}$Ga or other source-generated positron beam constrained by the 3 T or other magnetic field penetrates objects placed within the scanner. With the divergence of the beam magnetically constrained, the PET camera detects the positrons within the object rather than their transmission through the object. The resulting annihilation distribution is tomographically imaged by the PET camera. Under certain conditions, this image may be decomposed into maps of the positron beam's flux and material characteristic linear attenuation coefficient without need for auxiliary measurements or complete penetration of the beam through the object.

The attenuation of $\beta^+$-rays in matter is a complex process involving inelastic electron scattering, elastic nuclear scattering, the formation of positronium, and ultimately, positron-electron annihilation. Measurements related to these interactions may provide useful information on material properties, such as the characterization of defect distributions in solids by positron lifetime spectroscopy. Estimates of positron transport characteristics, such as their ranges, linear attenuation coefficients, and stopping powers in known materials, may be made. These transport characteristics may have various applications, such as PET images for diagnosis, radiation shielding, and dosimetry. Three-dimensional, non-destructive imaging of $\beta^+$-ray interaction cross-sections in heterogeneous materials may assist in other applications, such as any materials testing.

Figure 1:
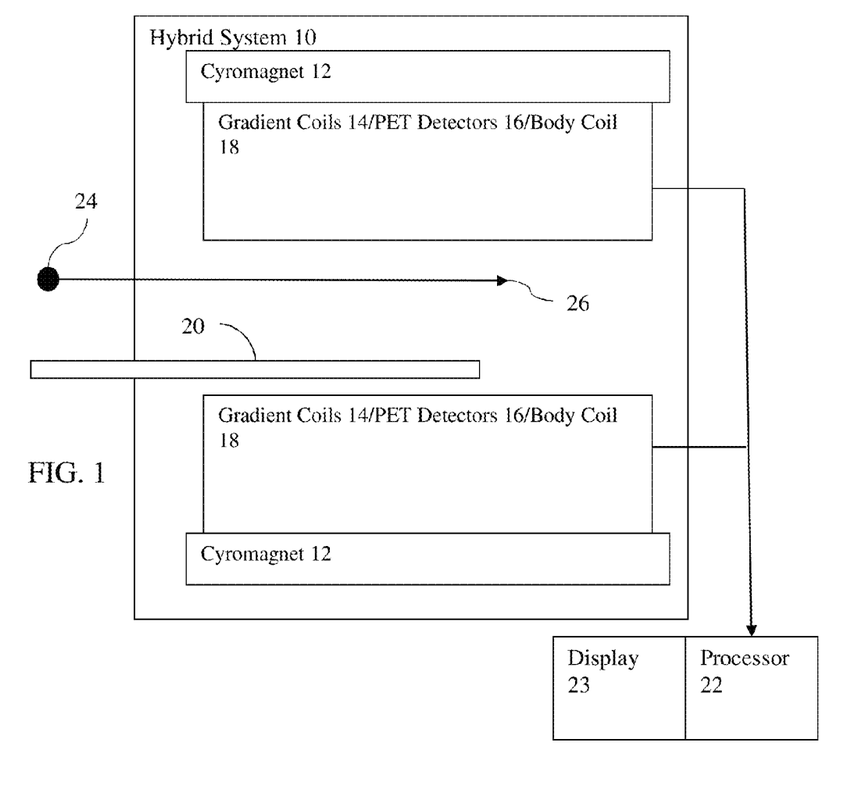
FIG. 1 is a block diagram of one embodiment of a hybrid PET/MR system.

FIG. 1 shows a positron attenuation tomography system. The system uses a hybrid magnetic resonance (MR) and positron emission tomography (PET) system 10. The hybrid PET/MR system 10 shown includes PET and MR portions. Only parts of the PET portion and parts of the MR portion are shown. Additional, different, or fewer components may be provided. In other embodiments, the positron attenuation tomography system does not include the MR imager, but instead uses another source of magnetic fields.

The PET and MR portions other than the processor 22 and display 24 shown are integrated into one device or within a common housing. The parts of the hybrid system 10 shown in FIG. 1 are in a single freestanding unit. In other embodiments, components of the hybrid PET/MR system 10 shown in FIG. 1 are in separate housings or separate freestanding units. The processor 22 communicates with data acquisition units of the PET portion through a filter plate for routing communications and power through the RF cabin for housing the MR portion.

A magnet, such as a cryomagnet 12, is used to create the positron beam. In the embodiment of FIG. 1, the magnet is the main field (i.e., $B_0$) magnet of a magnetic resonance imager. Any magnet may be used. The magnet is 1 or more tesla in strength, such as being 3 T or 9 T. The cryomagnet 12 generates a strong static main magnetic field $B_0$ in the range of, for example, 0.2 Tesla to 3 Tesla or more. The main magnetic field $B_0$ is approximately homogeneous in the field of view. The main magnetic field $B_0$ extends throughout the RF cabin along magnetic field lines. Different regions within the RF cabin may be subjected to stronger or weaker magnetic fields. For example, the ends of the cryomagnet 12 may have weaker magnetic field strength, but still be within the magnetic field $B_0$.

The magnet has any orientation or position relative to the object being examined. The positrons will travel in either direction along the field lines. The magnet generates a magnetic field through an object to be scanned, such as through the patient. The magnetic field establishes uniform field lines along which the positrons emitted from the source 24 travel in a helical path.

The MR portion of the hybrid system is shown as the cryomagnet 12, gradient coils 14, body coil 18, and patient bed 20. Additional, different, or fewer components may be provided. For example, a platform for testing materials instead of the bed 20 for the patient is provided. Other parts of the MR portion may be provided within a same housing, within a same room (e.g., within the radio frequency cabin), or within a same facility. The other parts of the MR portion may include local coils, cooling systems, pulse generation systems, image-processing systems, and user interface systems. The location of the different components of the MR portion is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate. In other embodiments, just the cryomagnet 12 is provided without the rest of the MR portion as MR imaging may not be used. The gradient coils 14 and body coil 18 are not provided.

The cryomagnet 12, gradient coils 14, and body coil 18 are in the RF cabin, such as a room isolated by a Faraday cage. The MR portion is configured to have a tubular or laterally open examination subject bore enclosing a field of view. The patient bed 20 (e.g., a patient gurney or table) supports an examination subject such as a patient. The patient bed 20 may be moved into the examination subject bore in order to generate images of the patient.

In one embodiment, the MR portion shares the bore with the PET portion. The object to be examined (e.g., the patient or other materials) is placed within the common bore or examination region. In alternative embodiments, the object is placed in a bore or examination region of the PET portion not shared with the MR portion. Instead, the magnetic field lines from the magnet 12 are established through the object without the object being in the bore of the magnet 12.

To generate a positron beam 26 in the object, a positron source 24 is positioned relative to the magnetic field so that a positron beam 26 extends into the object. The positron source 24 is held by a plastic or other material bracket relative to the bore, such as being held outside a field of view of the PET detectors 16 but within a cylindrical volume created by the bore. The source 24 is placed along a centerline of the bore or object, but may be offset. The positron source 24 is outside of the patient or object being scanned. In other embodiments, the positron source 24 is positioned outside the object, but within the field of view of the PET detectors 16. The source 24 is positioned so that the magnetic field lines passing through the source 24 also pass through the object.

Any positron source 24 may be used. Any $\beta^+$-emitting radioactive material, such as $^{18}$F, $^{120}$I, or $^{68}$Ga, may be used. Combinations of material may be used. A particle accelerator, such as a betatron, synchrotron, cyclotron, or linear accelerator, may be used to generate the source. The source has any size or shape. For example, the source 24 is formed as one or more rods stacked together or separated from each other. A point source or disk source may be used. The source is sized and shaped to provide positrons traveling along lines, planes or a volume of any size. For example, the source 24 creates positrons that will contact an entire surface of the object being scanned. Alternatively, the positron beam intersects with only a portion of the surface. In yet other embodiments, the source 24 may be moved or repositioned to scan or detect positron attenuation at different locations on the object.

The source 24 is shielded. Lead, tungsten, or other shielding is used. The shielding limits or prevents positrons from exiting the source 24 other than towards the object. Some or no shielding is provided for a surface of the source 24 directed towards the object.

Figure 2:
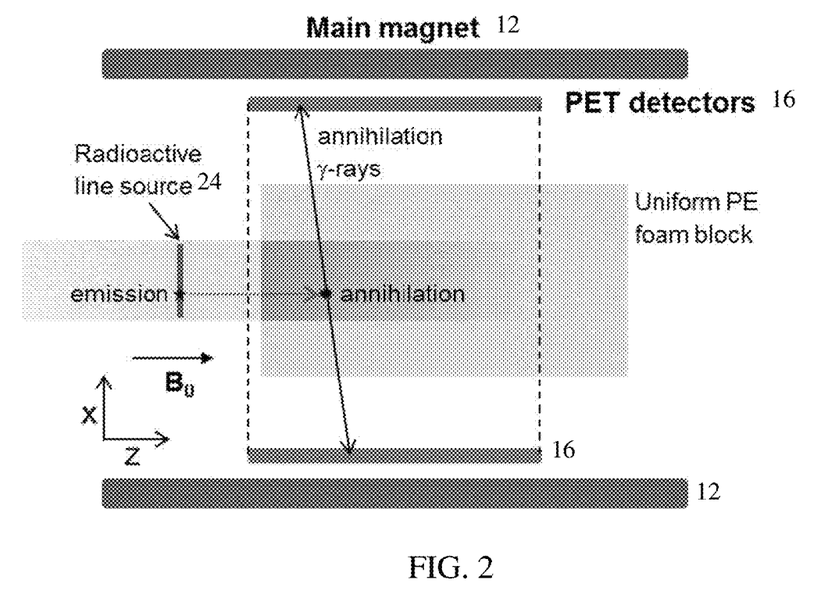
FIG. 2 illustrates PET detection of an emission from a positron source.

FIG. 2 shows a foam block positioned in the bore with the positron source 24 positioned outside the field of view of the PET detectors 16 such that the positron beam 26 passes into the foam block. The positron beam 26 travels along the magnetic field lines of the magnet 12 to pass into the object.

In one embodiment, the beam sources 24 are two 14.5 cm long, 3 mm diameter lines of bare hardened epoxy resin containing about 19 MBq of $^{68}$Ge/$^{68}$Ga radioactivity each (Emax=1.90 MeV). Greater or lesser doses and energies may be provided. In the example of FIG. 2, the sources 24 are placed approximately 15 cm outside the edge of the PET's axial FOV near its transverse center and stacked vertically, giving a horizontal planar beam over 6 mm thick and 14.5 cm wide extending across the PET's FOV.

The PET portion is a PET system configured to detect annihilation events of the positron beam interacting with the object. Annihilation events occur when a positron interacts with an electron. The PET system detects the rate or count of such interactions within the object.

The PET portion is shown as the PET detectors 16. Additional, different, or fewer components may be provided. Other parts of the PET portion may include data acquisition units (DAUs), power supplies, communications systems, image processing systems, tomography generation systems, and user interface systems. Any now known or later developed PET imaging system may be used. The location of the different components of the PET portion is within or outside the RF cabin, such as the image processing, tomography, power generation, and user interface components being outside the RF cabin. Power cables and fiber optic cables for communications connect the DAUs with the components outside the RF cabin through a filter plate.

The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

The detectors 16 are arranged individually or in groups in the bore of the MR portion. A ring of detectors in groups defines a field of view. The ring has a cylinder shape that encompasses the bore or location for placement of the object being scanned. For example, the PET detectors 16 have a 26 cm axial field of view centered within the 45 cm long uniform field region of the main magnet 12. The nominal spatial resolution near the center of the field of view is 4.2 mm, but greater or lesser resolution may be provided.

The detectors 16 generate three analog signals, two position signals and one energy signal. Each of the signals is output as a differential signal pair. Signals from the PET detectors 16 are directly digitized. Analog position and energy signals are filtered, amplified, and digitized inside the RF cabin, but may be digitized outside the RF cabin.

The PET portion, such as using the processor 22, reconstructs the detected events into a spatial representation. The detections along the various lines of response or detector pairs are tomographically reconstructed to determine the likely locations at which annihilation events occurred. Any reconstruction may be used, such as filtered back projection, maximum likelihood-expectation maximization, or ordered subsets expectation maximization. The reconstruction provides an annihilation rate per spatial location over a given period.

When a ~1 MeV β$^+$-decay source (e.g., $^{68}$Ga) is exposed within the field of the magnet 12, the emitted positrons follow helical paths around the field lines with gyroradii on the order of 1 mm due to the action of the Lorentz force. As a result, a non-diverging positron beam 26 is formed parallel to $B_0$ across the PET's field of view. Losses in air are modest (~1%/cm) and thus a vacuum system is not required for beam transport. The PET portion may accurately image the annihilation rate along the beam 26 within an object (e.g., foam block) intersecting the beam 26 by detecting the generated annihilation radiation.

The processor 22 is a computer, controller, server, application specific integrated circuit, field programmable gate array, graphics processing unit, digital circuit, analog circuit, or combinations thereof. In one embodiment, the processor 22 is a computer that is part of the PET system, but a separate component may be used. The processor 22 reconstructs the received PET signals.

The processor 22 is also configured to determine the positron attenuation. The PET detectors 16 detect annihilation per unit time along lines of response. Upon reconstruction, a count or annihilation rate per voxel is provided. This annihilation rate may be understood as the product of the positron flux and the linear attenuation coefficient of the material at that point. Since the only loss mechanism of positrons from the beam 26 is annihilation with an electron, if the beam 26 is fully stopped within the field of view of the PET detectors 16, the positron flux at any point may be estimated from the integral of annihilation rate down-beam from that point. This allows the flux and positron attenuation components of the annihilation rate image to be distinguished, providing for positron attenuation tomography. The positron attenuation is determined by calculation using emissions measured by the positron emission tomography system in response to the transmitted beam 26 of positrons into the patient or object. The spatial distribution of the annihilation events along the beam 26 in the object is used by the processor 22 to estimate the positron attenuation or attenuations along the beam 26.

The processor 22 estimates the linear attenuation coefficients of the object independent of flux of the positron beam 26 at the source 24. The energy or amount of radiation transmitted to the object does not need to be known. By having the beam 26 terminate in the object or in an object positioned behind the object being scanned, the integration of rate of annihilation along the beam may be used to estimate the attenuation at different locations.

The positron attenuation is estimated for the different locations along the beam 26 as a ratio of the annihilation event rate detected by the PET detectors 16 and provided in the reconstruction at each location, to the flux at that location. The flux passing through each of the locations in the object along the positron beam 26 is equal to the flux passing through a previous, up-beam location minus the annihilation event rate between the two locations. Where the positron beam 26 terminates in the object, the flux may be estimated for the different locations in the object along or prior to the termination of the positron beam 26 from the sum of all the annihilations along the positron beam 26 between the location and the termination point. The processor 22 determines the positron attenuation flux by an integration of the attenuations along the beam within the object or patient.

A positron beam 26 produced by an external beta-decay source 24 passes through the scanner, and maintains a macroscopic steady state positron distribution in a stationary object placed within the field of view. Let f(r, v) represent the number of positrons per unit phase space volume at (r, v), where r=(x, y, z) and v=($v_x$, $v_y$, $v_z$) are spatial position and velocity vectors respectively. If transverse diffusion of the beam due to scattering is neglected, the velocity-integrated transport equation for the positrons is reduced to:

$$\frac{\partial \phi_z(r)}{\partial z} = -\mu_z(r)\varphi_z(r) \tag{1}$$

where $\phi_z = \int v_z f(r, v) \, dv$ is the net velocity-integrated positron flux in the axial (z) direction, and $\mu_z(r)$ is an attenuation coefficient relative to this axial flux:

$$\mu_z(r) = \frac{\phi(r)}{\phi_z(r)}\left(\frac{\rho_e(r)}{\phi(r)} \int \sigma_{an}(r, v) v f(r, v) dv\right) \tag{2}$$

where $\phi(r) = \int v f(r, v) dv$ is the total velocity-integrated flux, $v = \|v\|$, $\rho_e(r)$ is the electron density, and $\sigma_{an}(r, v)$ is the electron-positron annihilation cross-section. The factor in brackets on the right is the total flux-weighted average macroscopic annihilation cross-section of the material for the beam. In conventional narrow-beam transport scenarios, the axial flux is attenuated by both scattering of particles out of the beam and their absorption within it. Here, due to the magnetic confinement, only absorption (annihilation) contributes to beam loss, but this loss is incurred by the total flux rather than just its axial component, resulting in the flux-ratio pre-factor in equation (2). As a consequence of this magnetic constraint, the material linear attenuation coefficients accessible to positron attenuation tomography may differ from those measured by other techniques.

The product $\mu_z(r)\phi_z(r)$ is equal to the annihilation rate density, $\lambda(r)$, estimated by PET. Assuming the beam propagates in the positive z direction and is fully absorbed by the point $z_0(x, y)$ within the PET field of view, integrating equation (1) from z to $z_0$ and substituting $\lambda = \mu_z \phi_z$ yields:

$$\phi(r) = \int_z^{z_0} \lambda(r') dz' \tag{3}$$

$$\mu_z(r) = \lambda(r)[\int_z^{z_0} \lambda(r') dz']^{-1}, \; z < z_0(x, y) \tag{4}$$

and thus both $\phi_z(r)$ and $\mu_z(r)$ are determined from the measured image data $\lambda(r)$ everywhere these data are non-zero.

As the beam penetrates a uniform object, the measured $\mu_z(r)$ increases with depth. For a $^{68}$Ga generated beam in a polyethylene (PE) foam block, the measured linear attenuation coefficient increases by about a factor of 4 as the beam is attenuated by a factor of $10^{-1}$. This differs from the reported quasi-exponential attenuation of unconstrained β-rays in matter measured using conventional differential transmission techniques. This variation may be due to changes in the velocity distribution of the flux. Simulations show that the total to axial flux ratio factor in equation (2) decreases from about 3.0 to 2.0 over this range, which would tend to decrease rather than increase the linear attenuation coefficient. On the other hand, the positron distribution moves to lower energies as the beam penetrates matter. The initial $^{68}$Ga β$^+$-decay source spectrum is broadly peaked between zero and its maximum emission energy of 1.9 MeV, with a mean energy of 796 keV. This degrades to 598 keV after 0.1 g/cm$^2$, and to 354 keV at 0.52 g/cm$^2$. The increase in the linear attenuation coefficient may be due to this 'softening' of the beam 26 as the beam 26 penetrates an object.

The detected attenuation coefficients may be used without beam-softening correction, but beam softening is used in another embodiment. The beam-softening correction may make the positron attenuation estimates less dependent on the beam characteristics. Contrary to expectations, magnetically constrained) β-rays are not exponentially attenuated. The effective attenuation coefficient increases with depth, as if the energy spectrum were getting 'softer.' If the softening depends only on the amount of attenuation as characterized by:

$$\bar{\mu}_z(r) = \int_0^z \mu_z(r') dz' \tag{5}$$

then a correction may be made as:

$$\mu'_z(r) = \mu z / F[\bar{\mu}_z(r)] \tag{6}$$

where F[ ] is a quadratic function. This reduces the beam dependence of the positron attenuation coefficients.

Other corrections may be performed. For example, a complication arises when the beam 26 passes through inhomogeneous materials, such as Al or Cu foils embedded in polymer foam or inhomogeneous tissue of a patient. Enhanced backscattering from the higher Z atoms within the foils increases beam intensity immediately up-beam from the foil, and thereby changes the apparent positron attenuation in this region. In such cases, additional measurements may help estimate more consistent positron attenuations. Any additional measurements may be made, such as measurements use to provide attenuation correction for quantitative PET. These might include the use of beams having different energy spectra from different radioisotopes and/or multi-angle imaging.

Images of structured objects may depend on their orientation relative to the positron beam 26, due to the finite resolution of the PET scanner. This effect may be modeled, and thus possibly corrected via multi-angle imaging, thereby reducing artifacts and improving resolution. Attenuation estimates are acquired at different angles relative to the beam 26, by rotating the object relative to the beam 26 between acquisitions. Any number of angles may be used. A multi-angle reconstruction combines the measures acquired at various angles to make a better estimate. The combination of the reconstructed measures may be a simple average. Alternatively, the combination is in an iterative model-based approach. With a forward model of the image formation process, the forward model is used to predict the measured images at all angles. The prediction is compared to the measurement to get the deviation between them. A back-propagation algorithm (e.g., maximum likelihood) is then used to improve the original attenuation estimate. The process is repeated until convergence or a stop criterion is satisfied.

The processor 22 generates an image of the positron attenuation. The image is a cross-section. For example, attenuation is estimated for voxels distributed in three dimensions. An arbitrary planar region is extracted and used for imaging. Alternatively, a three-dimensional rendering is performed. The image represents the spatial distribution of the linear attenuation coefficients. In other embodiments, a graph of attenuation as a function of distance is generated. A table or single value of attenuation may be output.

Alternatively or additionally, the processor 22 relates the attenuation coefficients to material properties of the object. A look-up table may be used to identify a material or property of material given the linear attenuation coefficient. The identified property or material may be output with or without a representation of spatial distribution.

The display 23 is a CRT, LCD, plasma screen, projector, printer, or other display device. The display 23 outputs information to the user, such as an image and/or identified material properties. The display 23 is configured to create the output by the processor 22 storing an image or information in a display plane buffer.

Due to termination of the positron beam in the object, the attenuation image or attenuation information may be for a limited or partial region of the object. Mass thicknesses up to 0.52 g/cm$^2$ at spatial resolutions of a few millimeters may be imaged, but greater or lesser thickness and resolution may be provided. In one embodiment, uniform polymer foam blocks are used to absorb the beam 26 after passing through the object of interest. Data acquisition times may be 1000-1500 sec per scan, but other periods may be used. The 511 keV annihilation photon data collected by the PET camera are reconstructed into an array with a voxel size of 2.03 mm axially and 2.09 mm in the transverse plane, using a standard maximum likelihood iterative algorithm. No corrections for the attenuation or scatter of the annihilation radiation are used because the attenuation of 511 keV γ-rays are approximately 100 times smaller than those of the positron beams. Corrections for the attenuation or scatter of the annihilation radiation may be used in alternative embodiments.

Figure 3:
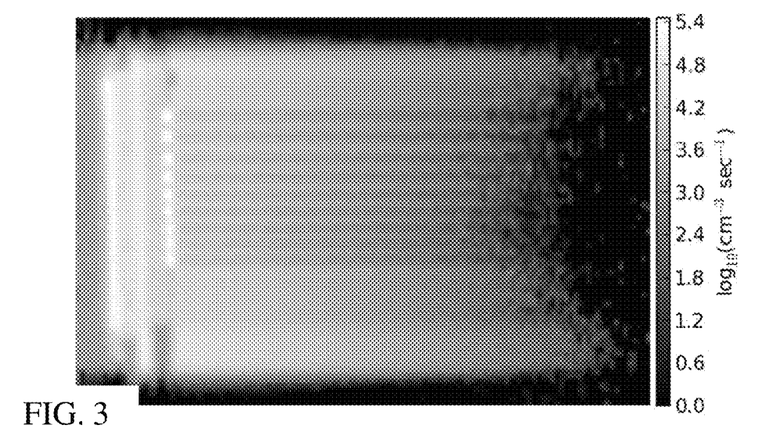
FIG. 3 is an example cross-sectional image of the PET annihilation rate density for a positron beam.

FIG. 3 shows the logarithm of the positron annihilation rate density in a test phantom as imaged by the PET system. The beam enters from the left and produces annihilation in air before it enters the phantom. The phantom has six material regions from left to right: plasticized tape, polystyrene (PS) foam (1 cm), balsa wood (3 mm), PS foam (1 cm), an array of nine plastic pieces, and a large uniform PE foam block of density 0.033 g/cm$^3$. The two 1 cm PS foam pieces are of similar density. The plastic pieces are sections of cable ties with their long axes normal to the plane of the image. Each piece is 1 mm thick and 5 mm wide. The eight spaces between the pieces are 5, 5, 4, 4, 3, 3, 2 and 2 mm in order from top to bottom. The shadows of these pieces extend to their right, remaining distinct over the full range of the beam. The beam-to-shadow contrast increases with penetration depth due to the beam softening effect.

Figure 4:
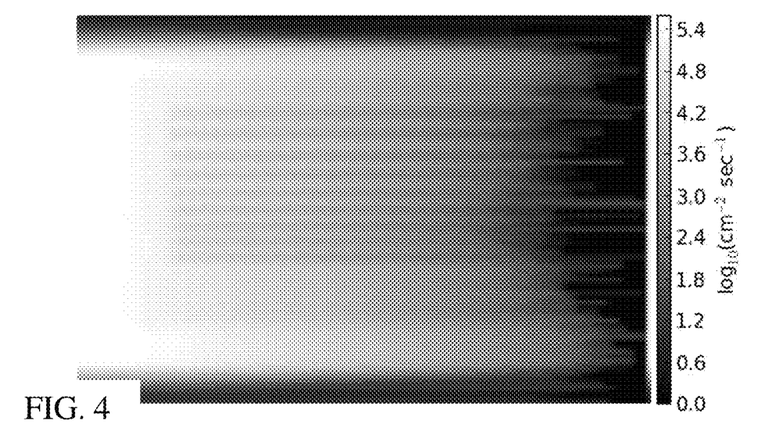
FIG. 4 is an example cross-sectional image of the positron flux for the positron beam of FIG. 3.
Figure 5:
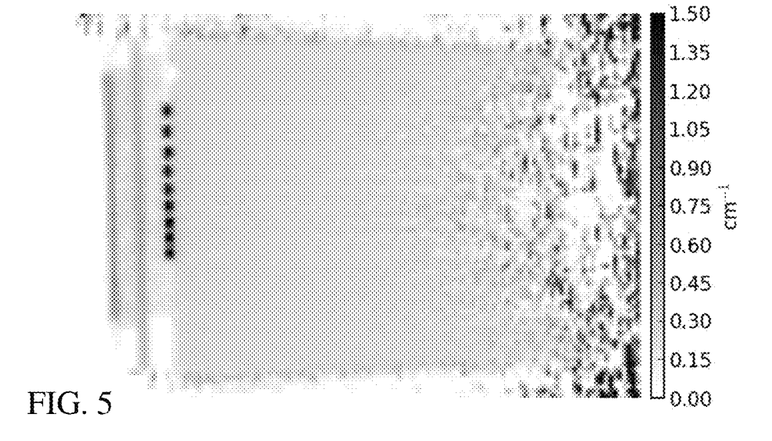
FIG. 5 is an example cross-sectional image of estimated linear attenuation coefficient for positrons of the positron beam of FIG. 3.

FIG. 4 represents the positron flux within the object estimated from the integral transformation of equation (3) of the data in FIG. 3. FIG. 5 is the positron linear attenuation coefficient image formed from the ratio of the data shown in FIGS. 3 and 4, and corrected for beam softening. The mean linear attenuation coefficient value in the PE foam block is 0.240±0.01 cm$^{-1}$, which is 5% higher than the value reported for the same material, based on an exponential fit to the attenuation of a $^{68}$Ga pill source beam. The noisy region to the right is due to the statistical fluctuations in the annihilation rate density observed by the PET camera. The apparent narrowing of the beam with depth is likely due to the tapering off the beam intensity at the ends of the line sources, causing the beam to fall more rapidly to the background noise level. The gaps between the plastic pieces are resolved down to 2 mm. Minimal residual beam-softening effect is observed.

Figure 6:
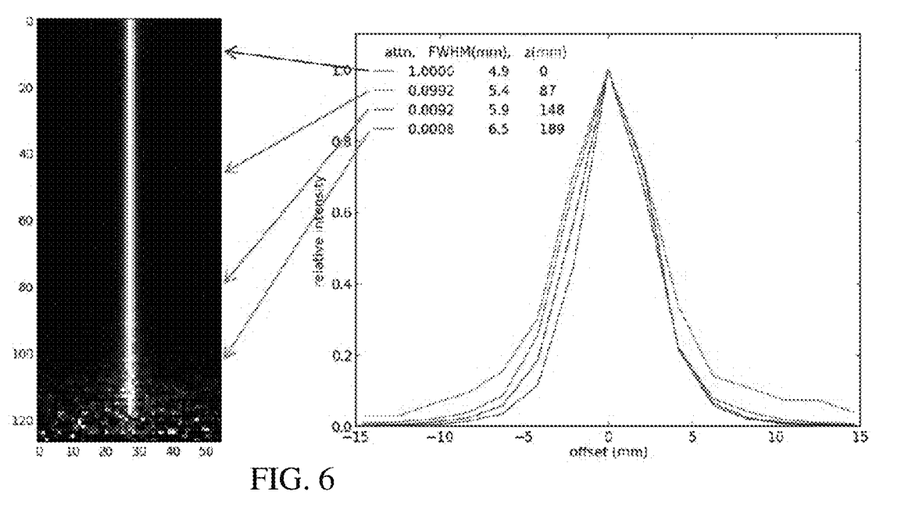
FIG. 6 is an example normalized image of a positron beam and relative intensity across cross-sections of the positron beam at different distances.
Figure 7:
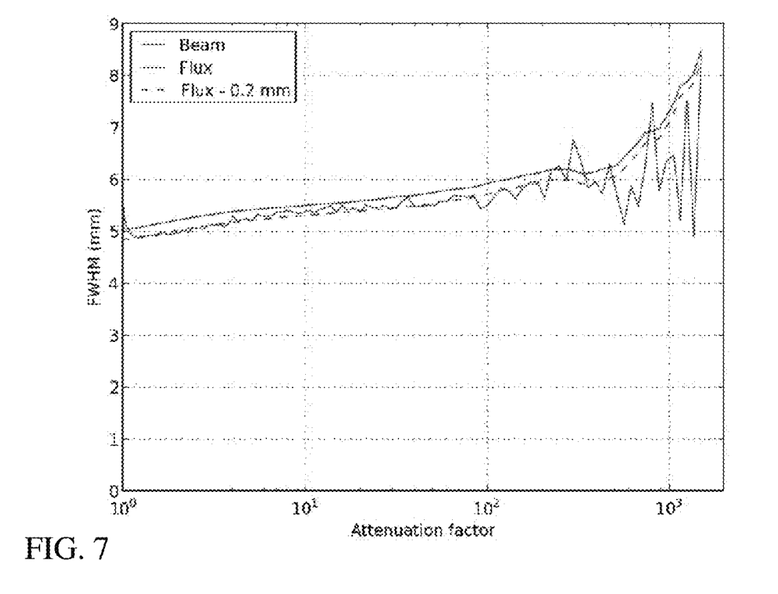
FIG. 7 is an example plot of full width at half maximum of the beam image and corresponding flux of FIG. 6.

Positron transport transverse to the magnetic field may be neglected. The beam/shadow structure in FIG. 3 seems to confirm that MeV positron beams in a 3 T field do largely maintain their transverse spatial coherence over nearly their full range, despite scattering. A quantitative assessment of the effect is shown in FIG. 6. FIG. 6 (left side) is an annihilation intensity image of a single 3 mm diameter line source beam in uniform PE foam viewed edge-on. The sagittal image planes within the beam are summed and each row of the summed image is normalized to the row's maximum value, removing the primary effect of attenuation. The full width at half maximum (FWHM) of transverse beam profiles in this image are evaluated versus depth and are plotted in FIG. 7. Four exemplary profiles are shown in FIG. 6 (right side). The asymmetry of the broadening may be due to a small misalignment between the PET image space and the magnetic field lines. The FWHM increase approximately linearly with attenuation, from 4.9 to 6.5 mm over a penetration depth of 18.9 cm and a flux attenuation factor of 10$^{-3}$. Monte Carlo simulations of a similar configuration confirm this beam coherence. The simulations show that a typical positron slows down mainly through small angle deflections that permit the positron to approximately maintain a helical path. Occasional large angle scattering events may move the gyrocenter by some appreciable fraction of the gyrodiameter, but there are too few such events to permit significant transverse dispersion.

The measured value of $\mu_z$ at a point z does not depend on the up-beam data, but only on whether the estimate of $\phi_z$ at that point, from the down-beam data, is consistent with $\lambda(z)$ in terms of lateral averaging. To assess this, the FWHMs of the positron flux computed from the annihilation intensity data in FIG. 6 are also plotted in FIG. 7. While both the $\lambda$ and $\phi_z$ distributions increase in width by about 30% over the full range, until near the end of the range the flux is only about 4% (0.2 mm) wider than the annihilation intensity at any point. The positron attenuation errors due to this discrepancy will depend on the annihilation intensity distribution but are likely to be small except at sharp lateral discontinuities in A.

Figure 8:
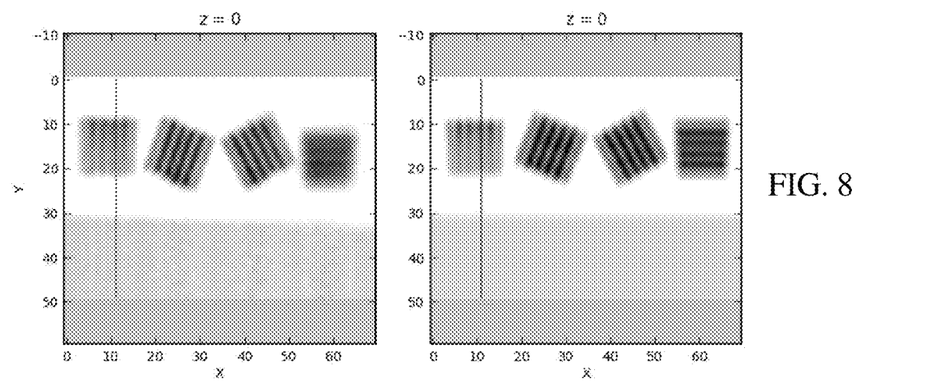
FIG. 8 show example measured (left) and modeled (right) positron attenuation images using directional imaging.
Figure 9:
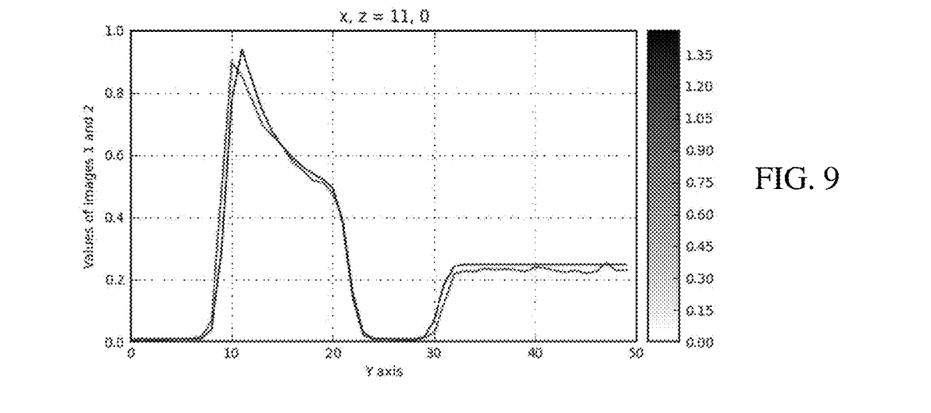
FIG. 9 shows a comparison of the images of FIG. 8.

Even if lateral transport of the positrons is neglected, the finite resolution of the PET camera, as well as the helical motion of the positrons in the beam, reduce the spatial accuracy of the observed data with respect to the basic relation $\lambda(r)=\mu_z(r)\phi_z(r)$. This is particularly consequential in the transverse direction. As a result, the estimated attenuation of an inhomogeneous object may depend on its orientation relative to the beam, particularly if the object being scanned contains finely spaced high-contrast parallel structures. A measured example is shown in FIG. 8 (left). Four 24 mm cubes each consisting of five 4.7 mm thick layers of polymer foam with paper backing between are imaged at orientations of 0°, 22°, −28° and 90° relative to the beam. The loss of spatial resolution and linear attenuation coefficient accuracy is most apparent when the layers are parallel to the beam. It is possible to model these effects along the following lines: a linear attenuation coefficient representation of the object is first smoothed transversely using a kernel approximating the helical component of the beam averaging; an annihilation intensity image is then estimated by propagating an axial flux through this modified object; this intensity distribution is then smoothed with a kernel representing the PET camera resolution and finally processed using the positron attenuation tomography transformation to yield a model image, as shown in FIG. 8 (right). FIG. 9 shows the values of the estimated attenuation along the lines in FIG. 8. The ability to make an accurate forward model of the imaging process, together with the redundancy of the data from multiple view angles, opens up the possibility of using iterative multi-angle image reconstruction techniques to correct artifacts and achieve improved spatial resolution.

Figure 10:
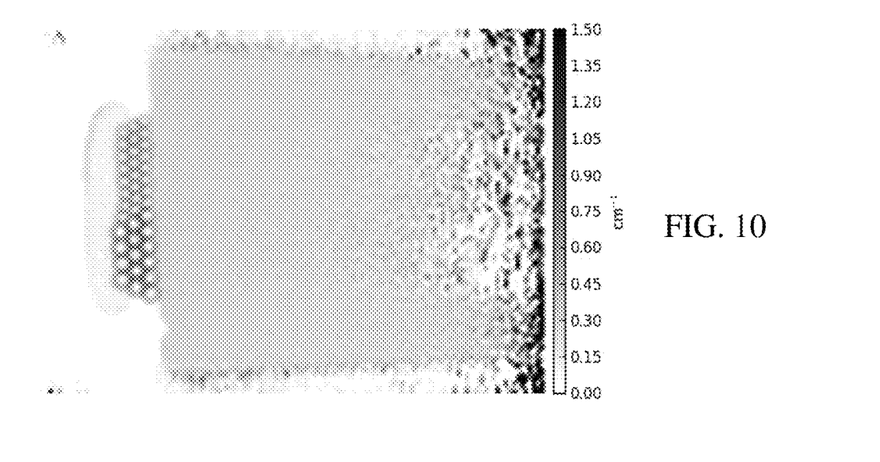
FIG. 10 is an example positron attenuation image of an array of straws on a foam block.
Figure 11:
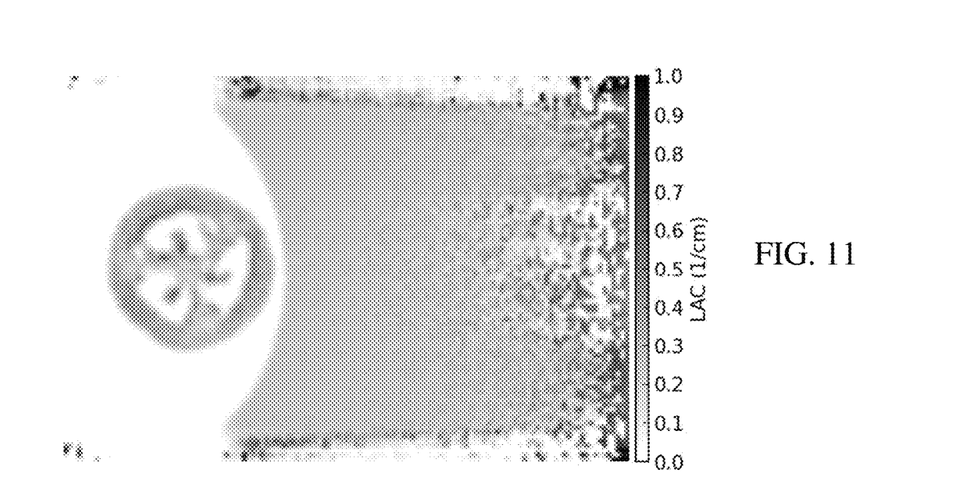
FIG. 11 is an example positron attenuation image of a luffa sponge adjacent a foam block.

Positron attenuation averaging artifacts in objects lacking linear structures oriented parallel to the beam direction are less obvious. FIG. 10 shows the estimated attenuation for an array of plastic soda straws with two diameters: 5.75 and 7.67 mm. A plastic bag filled with 3-5 mm diameter styrofoam beads is to their left. The surface of the plastic bag and the straw walls are resolved, although the beads and 1-2 mm gaps between straws are not. FIG. 11 shows a linear attenuation coefficient image cross-section of the dried fiber skeleton of a *Luffa aegyptiaca* fruit, 75 mm in diameter, in front of a curved PE foam block. This skeleton is composed of a thick network of cellulose-like fibers in air with a mean pore size of about one mm, and three larger air pockets. The estimated positron attenuation image shows mean density variations in this structure at a resolution of a few mm.

Positron attenuation tomography may be used to image positron annihilation cross-sections in three dimensions. The estimate of positron attenuation is self-calibrating, and transmission-less in that the near-surface regions of objects the beams do not fully penetrate may still be imaged. Higher energy β⁻-decay or accelerator sources may increase the depth of investigation. Higher strength magnet fields may improve the transverse resolution capability of the beams. Higher resolution MR-compatible PET detection systems may be used to improve resolution for estimated attenuation. For example, a BrainPET MR insert (Siemens) with 2.8 mm FWHM spatial resolution operating in a 9.4 T magnet may be used for PET imaging of $^{120}$I (Emax=4 MeV). Multiple view angle imaging may also improve resolution.

Practical applications of positron attenuation tomography may include medical diagnostics, materials science, biological research, radiation dosimetry or the study of the physics of positron beam propagation in matter. Positron attenuation estimation may be useful for validation of transport simulation codes (e.g., PENELOPE, or Geant4). Flux information may be provided.

Figure 12:
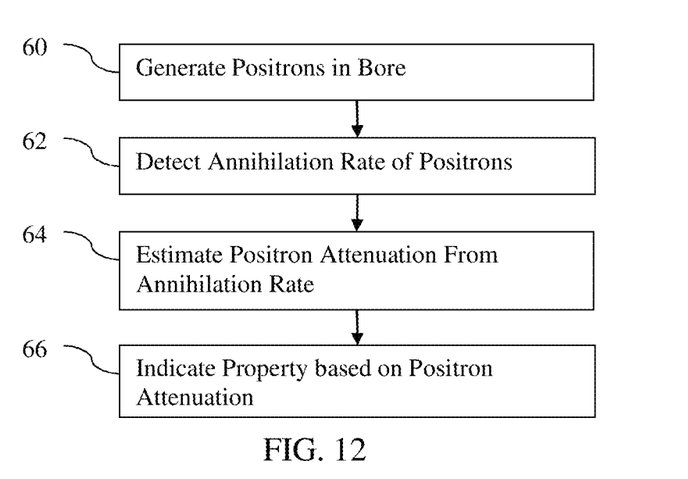
FIG. 12 is a flow chart diagram of an example embodiment of a method for positron attenuation tomography.

FIG. 12 shows one embodiment of a method for positron attenuation tomography. The method is implemented using the system 10 of FIG. 1, the system of FIG. 2, a computer, and/or other devices. For example, a magnet and positron source are used to generate positrons directed at material to be examined, PET detectors, such as in a PET system, are used to detect the annihilation rate, and a computer estimates the positron attenuation and indicates a material property based on the attenuation.

The method is performed in the order shown, but other orders may be used. For example, acts 60 and 62 are performed simultaneously. Additional, different, or fewer acts may be provided. For example, act 66 is not performed.

In act 60, positrons are directed along magnetic field lines through a bore of a ring of photon detectors or other PET detectors. A beam of any width or cross-section shape is generated in a magnetic field caused by the magnet. Emitted positrons from a source in the magnetic field travel along the magnetic field lines. By positioning the source relative to the field lines and the object being scanned, positrons are directed into the object by the Lorentz force.

The shielded positron source is placed outside the field of view of the photon detectors, but may be positioned inside the field of view. The source is fixed relative to the object to be scanned and the field lines, but may be moveable in other embodiments.

In act 62, an annihilation rate of the positrons in the material of the object is detected. The ring of photon detectors or other PET detectors detect the annihilation. At any given location in the material prior to termination of the beam, some of the positrons interact with electrons, resulting an in an annihilation. Each annihilation generates a pair of gamma rays traveling in generally opposite directions. The detectors detect the gamma rays. Relative timing is used to pair gamma rays, defining an event along a line of response. The events and lines of response may be used to determine the locations of the annihilations. After tomographic reconstruction, a count or annihilation rate for each voxel or location in the material is provided.

In act 64, a processor estimates the positron attenuation coefficient. The attenuation is estimated for one or more locations. For example, the attenuation is estimated for each of a plurality of locations through which the positrons pass before termination. The attenuation coefficient is estimated directionally along the magnetic field lines. The magnetic field causes the positrons to pass into the material being scanned, so the attenuation in that material for the locations along the positron beam is estimated. Different attenuations may be estimated for different locations.

The estimation is from the annihilation rate. A PET image of the reconstructed annihilation events is generated. For positron attenuation estimation, the detected annihilations that are used to generate the PET image are used to estimate the positron flux. The detected annihilation rate at a point is the product of the flux and the attenuation coefficient at that point. By integrating the annihilation rates represented in the PET image between different points along the path of the positrons in the material where the annihilation rate is greater than zero, the flux may be replaced with a function of the annihilation rate. As a result, the attenuation coefficient may be estimated from the annihilation rate only, such as the attenuation being a ratio of the annihilation rate to an integral of the annihilation rate between a given location and the location of the termination of the positron beam (i.e., first location along the positron beam 26 where the annihilation rate is zero).

A beam softening correction may be applied. Multiple-angle imaging may be used to reduce artifacts. Any combination of none, one, or more corrections may be used.

In act 66, a property of the material is indicated with the estimated positron attenuation coefficient. The processor indicates the property by presenting information on a display or otherwise providing the information. In one embodiment, the property is the attenuation itself. An average value of attenuation for a homogeneous material is output. Alternatively, a spatial distribution of the attenuation is output as an image. A one-dimensional graph, a two-dimensional cross-section image along any arbitrary plane, or a three-dimensional rendering of the attenuation is generated. The resulting image or graph shows different attenuations for different locations.

In another embodiment, the attenuation, with or without other information, is used to look up a property of the material. The derived material property is output as a value, graph, or image.

The indication may include other information, such as an MR image, PET image, computed tomography image, or combinations thereof. The material property indicated by the positron attenuation is provided separately, such as adjacently, or overlaid. For example, an MR image is displayed with attenuation being used to modulate the color and/or brightness of the MR image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A positron attenuation tomography system comprising:
    a magnet operable to generate a magnetic field through an object;
    a positron source positioned relative to the magnetic field so that a positron beam extends into the object, wherein the positron source is supported outside a field of view of the positron emission tomography system such that magnetic field lines of the magnetic field pass through the positron source and into the object;

a positron emission tomography system configured to detect annihilation events of the positron beam interacting with the object and to reconstruct a spatial distribution of the annihilation events; and a processor configured to estimate linear attenuation coefficients of the object along the positron beam from the spatial distribution of the annihilation events.

2. The system of claim 1 wherein the magnet is a main field magnet of a magnetic resonance imager.

3. The system of claim 2 wherein the magnetic resonance imager and the positron emission tomography system share a bore in which the object is placed.

4. The system of claim 1 wherein the positron source is a shielded source positioned along a center axis of a cylindrical ring of detectors of the positron emission tomography system, less shielding being on a side of the positron source facing the object.

5. The system of claim 1 wherein the positron emission tomography system is configured to detect the annihilation events caused by interaction of positrons of the positron beam with the object.

6. The system of claim 1 wherein the processor is configured to estimate the linear attenuation coefficients of the object independent of flux of the positron beam at the source.

7. The system of claim 1 wherein the processor is configured to estimate each of the linear attenuation coefficients for different locations along the positron beam in the object as a ratio of an annihilation event rate of the annihilation events to a flux for each of the locations.

8. The system of claim 7 wherein the flux passing a first of the locations in the object along the positron beam is equal to the flux passing through a second of the locations minus the annihilation event rate between the first and second points.

9. The system of claim 7 wherein the positron beam terminates in the object and wherein the processor is configured to estimate the flux from the different locations in the object prior to the termination of the positron beam.

10. The system of claim 1 wherein the processor is configured to relate the attenuation coefficients to material properties of the object;

further comprising a display configured to output the material properties.

11. The system of claim 1 wherein the processor is configured to generate an image of the attenuation coefficients of the object;

further comprising a display configured to display the image.

12. A method for positron attenuation tomography, the method comprising:

generating positrons directed along magnetic field lines through a bore of a ring of photon detectors, wherein generating comprises placing a positron source outside a field of view of the ring of photon detectors in a main field of a magnetic resonance imager;

detecting an annihilation rate for the positrons at a location in material with the ring of photon detectors;

estimating a positron attenuation coefficient for the location from the annihilation rate; and indicating a property of the material with the positron attenuation coefficient.

13. The method of claim 12 wherein estimating comprises estimating the positron attenuation coefficient directionally along the magnetic field lines.

14. The method of claim 12 wherein estimating the positron attenuation coefficient comprises integrating the annihilation rate along a path of the positrons in the object where the annihilation rate is greater than zero.

15. The method of claim 12 wherein indicating comprises generating an image of the material, the positron attenuation coefficient for the location represented in the image.

16. A hybrid magnetic resonance and positron emission tomography system comprising:

a bore shared by a magnetic resonance system having a magnetic field and a positron emission tomography system;

a positron source supported outside a field of view of the positron emission tomography system such that magnetic field lines of the magnetic field pass through the positron source and into a patient within the bore; and a processor configured to determine positron attenuation in the patient within the bore, the positron attenuation determined by calculation using emissions measured by the positron emission tomography system in response to a transmitted beam of positrons into the patient.

17. The hybrid magnetic resonance and positron emission tomography system of claim 16 further comprising a positron source positioned by or in the bore such that the beam of positron travels along magnetic field lines of the magnetic resonance system.

18. The hybrid magnetic resonance and positron emission tomography system of claim 16 wherein the processor is configured to determine the positron attenuation as a function of an integration of the emissions along the beam within the patient.

* * * * *